US009657029B2

(12) United States Patent
Sun (10) Patent No.: US 9,657,029 B2
(45) Date of Patent: May 23, 2017

(54) METHOD OF PREPARING OXYMORPHONE (71) Applicant: SIEGFRIED AG, Zofingen (CH)

(72) Inventor: Jianguang Sun, Hamilton, NJ (US)

(73) Assignee: Siegfried Generics International AG, Zofingen (CH)

( * ) Notice: Subject to any disclaimer, the term of this patent is extended or adjusted under 35 U.S.C. 154(b) by 0 days.

(21) Appl. No.: 14/406,259

(22) PCT Filed: Jun. 11, 2013

(86) PCT No.: PCT/US2013/045198
§ 371 (c)(1),
(2) Date: Dec. 8, 2014

(87) PCT Pub. No.: WO2013/188418
PCT Pub. Date: Dec. 19, 2013

(65) Prior Publication Data
US 2015/0133484 A1    May 14, 2015

Related U.S. Application Data (60) Provisional application No. 61/657,905, filed on Jun. 11, 2012.

(51) Int. Cl.
C07D 489/04    (2006.01)
C07D 489/08    (2006.01)
C07D 489/02    (2006.01)

(52) U.S. Cl.
CPC ......... C07D 489/08 (2013.01); C07D 489/02 (2013.01)

(58) Field of Classification Search
USPC ..................... 514/282; 546/45, 44
See application file for complete search history.

(56) References Cited

U.S. PATENT DOCUMENTS

| 7,851,482 | B2 | 12/2010 | Dung et al. | |
| 8,134,002 | B2 * | 3/2012 | Huang | C07D 489/08 546/44 |
| 8,309,727 | B2 * | 11/2012 | Wang | C07D 489/02 546/44 |
| 2008/0146601 | A1 | 6/2008 | Dung et al. | |
| 2010/0048905 | A1 | 2/2010 | Wang et al. | |
| 2013/0035489 | A1 | 2/2013 | Weber et al. | |

FOREIGN PATENT DOCUMENTS

WO    WO 2008/048711    4/2008

OTHER PUBLICATIONS

Notification of Transmittal of the International Search Report and the Written Opinion of the International Searching Authority, or the Declaration, corresponding to International application PCT/US2013/045198 mailed Aug. 27, 2013.
Notification of Transmittal of the International Preliminary Report on Patentability (Chapter 1 of the Patent Cooperation Treaty) corresponding to International application PCT/US2013/045198 mailed Dec. 24, 2014.

* cited by examiner

Primary Examiner — Charanjit Aulakh
(74) Attorney, Agent, or Firm — Jenkins, Wilson, Taylor & Hunt, P.A.

(57) ABSTRACT

The invention relates to an improved method of preparing oxymorphone or a salt thereof from oripavine. In particular, the invention relates to a method of preparing oxymorphone with a content of alpha-beta-unsaturated ketones (ABUK) <10 ppm, wherein the content of 8,14-dihydroxydihydromorphinone in the prepared oxymorphone is >10 ppm.

16 Claims, 2 Drawing Sheets

METHOD OF PREPARING OXYMORPHONE

CROSS-REFERENCE TO RELATED APPLICATIONS

This application claims benefit of U.S. Provisional Application Ser. No. 61/657,905 filed Jun. 11, 2012, the disclosure of which is herein incorporated by reference in its entirety.

FIELD OF THE INVENTION

The invention relates to an improved method of preparing oxymorphone or a salt thereof from oripavine. In particular, the invention relates to a method of preparing oxymorphone with a content of alpha-beta-unsaturated ketones (ABUK) <10 ppm, wherein the content of 8,14-dihydroxydihydromorphinone in the prepared oxymorphone is >10 ppm.

BACKGROUND

Oxymorphone, generally administered in the form of its hydrochloride salt, is a potent semi-synthetic opiate analgesic, for the relief of moderate to severe pain, and has been approved for use since 1959. It can be administered as an injectable solution, suppository, tablet or extended release tablet. It is desirable to develop high purity forms of oxymorphone, especially with low levels of alpha-beta-unsaturated ketones, and a method for its synthesis.

Several methods for synthesizing oxymorphone from compounds isolated from the opium poppy or compounds derived therefrom are known, for example, starting from morphine, thebaine, or from oxycodone.

WO 2008/048711 describes a process for preparing oxymorphone wherein oripavine is oxidized to 14-hydroxymorphinone in a first step and 14-hydroxymorphinone is then reduced with hydrogen gas in the presence of a catalyst. Afterwards, oxymorphone is precipitated as a free base. The base is then further purified, and afterwards the HCl salt of oxymorphone is formed.

In US 2008/0146601, a process for the purification of a prepared raw oxymorphone is presented wherein the produced oxymorphone has a content of alpha-beta-unsaturated ketones <10 ppm. For the purification of the crude oxymorphone which is obtained in a similar fashion as in WO 2008/048711, a further hydrogenation of the crude oxymorphone is required. In this procedure, expensive high pressure equipment is needed for the hydrogenation step of the crude oxymorphone.

A further method for preparing oxymorphone is disclosed in US 2010/0048905. In the process described therein, the oxidation reaction of oripavine is carried out in the presence of a strong acid for an accelerated reaction, and then the reduction is carried out utilizing a hydrogen transfer reagent. A drawback of this process is that the strong acid utilized in the oxidation reaction has to be neutralized in the reduction step, leading to further by-products which affect the purity of the produced oxymorphone. Also, the reaction is slow, thereby limiting the productivity of the whole process.

There, thus, remains a need for methods which permit the formation of oxymorphone with low contamination of alpha-beta unsaturated ketones in a fast and efficient way which do not require a tedious and equipment-intensive purification treatment of crude oxymorphone.

SUMMARY OF THE INVENTION

A problem of the presently known methods of preparing oxymorphone is that the preparation of oxymorphone with a low content of alpha-beta-unsaturated ketones <10 ppm still requires a long time and is complicated. Further, the cleaning and purification of the product is tedious and requires expensive equipment for a hydrogenation under pressure.

The object of the present invention is therefore to provide an improved method of obtaining oxymorphone or its salt with reduced levels of alpha-beta-unsaturated ketones that do not require a tedious and complicated workup of an intermediate oxymorphone.

The present inventors have found that oxymorphone or a salt thereof can be produced with reduced levels of alpha-beta-unsaturated ketones without the use of a strong acid.

In one aspect, the present invention provides for a method of preparing oxymorphone or a salt thereof, comprising:
  i) oxidizing oripavine to obtain 14-hydroxymorphinone;
  ii) reducing the 14-hydroxymorphinone to obtain oxymorphone; and optionally
  iii) producing an oxymorphone salt by treatment of the crude oxymorphone from ii) with an acid to produce an oxymorphone salt;
characterized in that the reducing step ii) proceeds without the use of strong acid.

Further embodiments are described in the dependent claims, as well as a product produced by the present method of the invention.

In a further aspect, the present invention discloses a composition comprising oxymorphone or a salt thereof, preferably oxymorphone HCl or oxymorphone base, characterized in that the content of alpha-beta-unsaturated ketones is <10 ppm and that the content of 8,14-dihydroxydihydromorphinone is >10 ppm.

BRIEF DESCRIPTION OF THE FIGURES

The invention will in the following be described with reference to figures which do, however, not restrict the scope of the invention.

DETAILED DESCRIPTION

Definitions

In the present invention, the term "alkyl" refers to linear or branched alkyl groups.

The term "aryl", as used herein, refers to aromatic residues.

All percentages indicated herein are by weight, unless specified differently.

A salt of oxymorphone is a salt that is obtained by reacting oxymorphone with an acid.

Transition metals catalysts are salts, metals, oxides or complexes in various forms of elements out of the groups III to XII.

The present invention provides for a method of preparing oxymorphone or a salt thereof, comprising:
  i) oxidizing oripavine to obtain 14-hydroxymorphinone;
  ii) reducing the 14-hydroxymorphinone to obtain oxymorphone; and optionally
  iii) producing an oxymorphone salt by treatment of the crude oxymorphone from ii) with an acid to produce an oxymorphone salt;
characterized in that the reducing step ii) proceeds without the use of strong acid.

A general reaction scheme 1 is shown below, which shows how the oxymorphone is formed in steps i) and ii) from oripavine:

In certain embodiments, the oxymorphone produced in step ii) and/or the oxymorphone salt produced in step iii) comprises less than 10 ppm alpha-beta unsaturated ketones.

Reaction scheme 1

The reaction scheme further shows that 8α-14-dihydroxydihydromorphinone and 8β-14-dihydroxydihydromorphinone are obtained as side products due to a reaction of 14-hydroxymorphinone with water present in the reaction, which further can react to other side products that can reduce the quality of the final product oxymorphone or a salt thereof. It has further been found that long holding periods of solutions of oxymorphone can lead to increased levels of 14-hydroxymorphinone, an alpha-beta-unsaturated ketone. This effect is especially showing at higher temperatures, in particular at the boiling point of the solvent.

Preferably water is present as a solvent in the present method. The water can thereby be present as a solvent for the oxidizing agent or be a co-solvent in one or more of the steps in the method.

In certain embodiments, the oxymorphone can be reacted with an acid to produce an oxymorphone salt, for example oxymorphone HCl.

Oxymorphone HCl

In certain embodiments, levels of >10 ppm, >25 ppm or >50 ppm, or >100 ppm, or >250 ppm, or 500 ppm and up to and including 1500 ppm of 8,14-dihydroxydihydromorphinone are allowed in the oxymorphone produced in step ii) and/or its salt produced in step iii), as these do not negatively influence the reaction. In certain embodiments, levels of ≤10 ppm of 8,14-dihydroxydihydromorphinone are allowed in the oxymorphone produced in step ii) and/or its salt produced in step iii). The levels of 8,14-dihydroxydihydromorphinone thereby can be controlled online via known detecting methods or by in process controls, e.g. by high-performance liquid chromatography (HPLC). In certain embodiments, the oxymorphone produced in step ii) and/or its salt produced in step iii) have a content of 8,14-dihydroxydihydromorphinone >10 ppm.

The production of an oxymorphone salt, e.g. oxymorphone HCl, as seen in the following scheme 2, can be accomplished by several reaction routes after the oxidizing step i). For example a hydrogenation, e.g. with hydrogen gas or a transfer hydrogenation, e.g. without introduction of hydrogen gas, can be carried out and then the oxymorphone salt is directly produced afterwards, as is exemplary shown in the left path of scheme 2 for oxymorphone HCl. Alternatively, a hydrogenation can be carried out to form the oxymorphone base, and then a hydrogenation, e.g. with hydrogen gas or a transfer hydrogenation, e.g. without introduction of hydrogen gas, can be carried out and the oxymorphone salt is produced afterwards, as is exemplary shown in the right path of scheme 2 for oxymorphone HCl.

Scheme 2

* Conventional Hydrogenation - With hydrogen gas
  Transfer Hydrogenation - Without introduction of hydrogen gas In certain embodiments, the reducing step ii) comprises a hydrogenation of the 14-hydroxymorphinone to obtain oxymorphone. In such embodiments, it is not necessary to carry out a second hydrogenation to produce oxymorphone or a salt thereof with low levels of ABUK, especially with less than 10 ppm alpha-beta unsaturated ketones. It is also possible to carry out a second hydrogenation, as shown above. However, it is preferred that no second hydrogenation is carried out, as this would involve further costs.

In certain embodiments, the oxymorphone salt is produced without prior isolation of oxymorphone as a free base after reducing step ii). In such preferred embodiments, levels of 14-hydroxymorphinone as an ABUK can be reduced, as long holding periods of solutions of oxymorphone can lead to increased levels of 14-hydroxymorphinone. Directly going to the base after the hydrogenation could lead to increased levels of 14-hydroxymorphinone.

In certain embodiments, the 14-hydroxymorphinone is not isolated before reducing step ii) as this is simpler in regard to the production procedure.

In the present method, oripavine is first oxidized in an oxidizing step i) to obtain 14-hydroxymorphinone. The oxidation is not limited and known in the art.

The oripavine can thereby be obtained from known sources. Preferably the oripavine is derived from concentrated poppy straw. Preferably the concentrated poppy straw is derived from a high oripavine yielding strain of poppy. It is also possible to use synthetic oripavine in the present method.

In certain embodiments, the oxidizing step i) is carried out in the presence of an oxidizing agent. The oripavine is preferably combined with a suitable amount of the oxidizing agent at a pH>1 in the reaction mixture. A preferred pH of the reaction mixture in the oxidizing step is between >1 and 4, and a further preferred pH is between 2 and 3. A most preferred pH is around 2.

Preferably, the oxidizing agent comprises a peroxy acid which can in certain embodiments be added to the oxidizing reaction or can be formed in situ. Preferably, the peroxy acid is formed in situ.

Preferred examples of the peroxy acid include $HCO_3H$, $CH_3CO_3H$, $m$-$ClC_6H_4CO_3H$, and $R^4CO_3H$ wherein $R^4$ is H, an alkyl group with 1 to 20 carbons that can be substituted or unsubstituted or an aryl group that can be substituted or unsubstituted. The peroxy acid can also be formed from the reaction of an acid according to formula $R^4CO_2H$ and an oxidant, wherein $R^4$ is H, an alkyl group with 1-20 carbons, or an aryl group. Preferably the concentration of the acid according to formula $R^4CO_2H$, in the whole mixture in step i), is >20 wt. %, more preferably between >20 wt. % and 60 wt. %, further preferably between 30 wt. % and 50 wt. %. In certain embodiments, the acid of formula $R^4CO_2H$ can also dissolve the oripavine and the products produced in step i) and/or step ii) and/or step iii). Further, the concentration of oripavine in the whole mixture in step i) is preferably >20 wt. %, more preferably between >20% and 40 wt. %, and further preferably between 23 wt. % and 33 wt. %.

In the mixture, also other solvents like water or an alcohol, for example ethanol, isopropanol can be present.

A preferred oxidant may be selected from the group consisting of, but not limited to, $H_2O_2$, $K_2O_2$, $Na_2O_2$, $Li_2O_2$, $Cs_2O_2$, $K_2SO_5$, $Na_2SO_5$, percarbonates, peroxodicarbonates, peroxocarbonates, perborates and perphosphates, preferably $H_2O_2$, $K_2O_2$, $Na_2O_2$, $Li_2O_2$, $Cs_2O_2$, $K_2SO_5$, $Na_2SO_5$, and mixtures thereof. A particularly preferred oxidant is $H_2O_2$.

If the peroxy acid is formed in situ, the oxidant can be added to the acid according to formula $R^4CO_2H$ in any known means. The oxidant can be added together with the acid in any known means. It can be added in one batch, in two portions, etc. Preferably it is added in portions so that the reaction can be carried out safely.

In a particularly preferred example, step i) is carried out in the absence of a strong acid with a pKa<0. Preferably the pKa of any acid used in step i) should be higher than 1, further preferably higher than 2 and particularly preferably higher than 3. Preferred acids that can be used in the oxidizing step i) are carboxylic acids and/or further organic acids like metachlorobenzoic acid, citric acid, formic acid, or acetic acid. Preferred are formic acid and acetic acid.

In a preferred embodiment, the oxidizing step i) is carried out at a temperature of 15 to 55° C. More preferably, the reaction is carried out at a temperature of 25 to 45° C., most preferred at a temperature of 30 to 35° C., in particular 30° C. The higher the reaction temperature, the faster impurities will form at the end of the reaction, and the reducing step should start sooner. Similarly, the equivalents of peroxide impact the rate of reaction. The acid and the oxidant can be of different concentration, and it is advisable to adjust the component concentrations accordingly.

Preferably, the reaction time in the oxidizing step i) is 1 to 24 hours, preferably 1 to 10 hours, more preferably 3 to 10 hours. Further preferred is a reaction time of 4 to 6 hours.

In general, it is however important to determine the time necessary for the reaction based on in-process testing of the reaction in step i). Thus the reaction completion should be monitored by in-process sampling or by on-line analysis, for example by, but not limited to, HPLC or on-line Raman analysis.

The second step in the present method is a reducing step for reducing the 14-hydroxymorphinone obtained in step i) to obtain oxymorphone as a base. Preferably, the reducing step ii) is carried out at a pH>1 in the reaction mixture. A preferred pH of the reaction mixture in the oxidizing step is between >1 and 4, and a further preferred pH is between 2 and 3. A most preferred pH is around 2.

In certain embodiments, the reducing step ii) comprises combining 14-hydroxymorphinone and a reducing agent absent a strong acid. Strong acids that should not be used in step ii) of the present invention include HCl, HBr, HI, HClO$_4$, HNO$_3$, H$_2$SO$_4$, CH$_3$SO$_3$H, H$_3$PO$_4$, p-toluenesulfonic acid, HClO$_3$, and mixtures thereof.

In preferred embodiments the reducing step ii) comprises combining 14-hydroxymorphinone and a reducing agent in formic acid and optionally alcohol. In other preferred embodiments the reducing step ii) comprises combining 14-hydroxymorphinone and a reducing agent in acetic acid. The alcohol is preferably isopropanol. Preferred is the use of formic acid with optionally alcohol, preferably isopropanol.

In certain embodiments, the reducing step comprises adding a hydrogen transfer agent, for example one as described e.g. in US 2010/0048905, which is incorporated herein in its entirety by reference. Preferably the hydrogen transfer agent is added without adding hydrogen. In certain embodiments, a catalyst is added to the hydrogen transfer agent, e.g. if the hydrogen transfer agent is formic acid or alcohol, e.g. isopropyl alcohol or isobutyl alcohol.

The hydrogen transfer reagent can be selected from the group consisting of isopropyl alcohol, isobutyl alcohol, HCO$_2$H, HCO$_2$H/HCO$_2$NH$_4$, HCO$_2$H/HCO$_2$Na, HCO$_2$H/NR$_3$, HCHO, HCHO/NR$_3$, or Hantzsch base, wherein R is independently selected from H, a substituted or unsubstituted alkyl group with 1-20 carbons, a substituted or unsubstituted aryl, or mixtures thereof, preferably from the group consisting of isopropyl alcohol, isobutyl alcohol, HCO$_2$H, HCO$_2$H/HCO$_2$NH$_4$, HCO$_2$H/HCO$_2$Na, HCO$_2$H/NR$_3$, HCHO, HCHO/NR$_3$, wherein R is defined as above.

A Hantzsch base is a 2-R$^a$ 3-R$^b$ 4-R$^c$ 5-R$^d$ 6-R$^e$ 1,4-dihydropyridine 3,5-dicarboxylate of the following formula:

wherein R$^a$, R$^b$, R$^d$ and R$^e$ are independently selected from aryl (which optionally can be substituted with C1-C8 alkyl, aryl and/or OH); linear, branched or cyclic C1-C8 alkyl which can be substituted with —OH, -aryl (which can optionally be substituted with C1-C8 alkyl, aryl and/or OH); linear, branched or cyclic C1-C8 alkenyl which can be substituted with —OH, -aryl (which can optionally be substituted with C1-C8 alkyl, aryl and/or OH), and wherein R$^c$ is selected from hydrogen, aryl (which optionally can be substituted with C1-C8 alkyl, aryl and/or OH); linear, branched or cyclic C1-C8 alkyl which can be substituted with —OH, -aryl (which can optionally be substituted with C1-C8 alkyl, aryl and/or OH); linear, branched or cyclic C1-C8 alkenyl which can be substituted with —OH, -aryl (which can optionally be substituted with C1-C8 alkyl, aryl and/or OH). A preferred Hantzsch base is 3,5-diethyl-2,6-dimethyl 1,4-dihydropyridine 3,5-dicarboxylate.

The reaction with a hydrogen transfer agent can be carried out in the presence or absence of oxygen. Furthermore, step ii) of reducing the 14-hydroxymorphinone can be carried out under substantially atmospheric pressure when using the hydrogen transfer agent.

Preferably, a metal catalyst selected from the group consisting of transition metals in any form on carbon, BaSO4, alumina, transition metal oxides and/or transition metal salts, phosphine ligand metal complexes, and mixtures thereof, preferably transition metals on carbon, transition metal oxides and/or transition metal salts, phosphine ligand metal complexes, and mixtures thereof, is present concomitant with the hydrogen transfer agent. A particular preferred example of the metal catalyst is Pd/C, palladium chloride or palladium nanoclusters. The amount of the catalyst is not particularly limited as long as it catalyzes the reaction. An exemplary catalyst is 5% Pd on carbon which can be added to the reaction mixture between 0.1 wt. % and 40 wt. %. The catalyst is preferably added in an amount between 0.1 wt. % to 10 wt %, more preferably in an amount from 1.0 wt. % to 5.0 wt. % on a dry basis.

It is also possible that hydrogen is added from an outside source while a hydrogen transfer agent is used.

In certain embodiments, the reducing step ii) can comprise a conventional hydrogenation. This conventional hydrogenation is also known to the skilled person, as described e.g. in WO 2008/048711 which is incorporated herein by reference in its entirety.

Preferably, the conventional hydrogenation is carried out with hydrogen in the presence of a metal catalyst selected from the group consisting of transition metals on carbon, transition metal oxides and/or transition metal salts, phosphine ligand metal complexes, and mixtures thereof. A particularly preferred example of the metal catalyst is Pd/C or palladium chloride. The amount of the catalyst is not particularly limited as long as it is capable of catalyzing the reaction. An exemplary catalyst is 5% Pd on carbon which can be added to the reaction mixture between 0.1 wt. % and 40 wt. %. The hydrogenation can be carried out at pressures for example as high as at 600 psi or higher, typically at a hydrogen pressure of 10 to 150 psi, preferably 40 to 50 psi.

When using a catalyst with the hydrogen transfer agent, and also when using a catalyst in the conventional hydrogenation, additional catalyst can be charged during the reducing step ii). This can preferably be done when the reduction reaction stalls. Preferably, the same catalyst is added as additional catalyst as was added for the reducing step before, but also two different catalysts can be added, preferably from the group consisting of transition metals on carbon, transition metal oxides and/or transition metal salts, phosphine ligand metal complexes, and mixtures thereof. In such a case a further reduction of ABUK is possible.

In a preferred embodiment, the reducing step ii) is carried out at a temperature of 10 to 110° C. or up to the boiling point of the solvent or solvent mixture, more preferably 10 to 95° C. More preferably, the reaction is carried out at a temperature of 15 to 95° C., more preferably at 15 to 75° C., more preferably at 15 to 55° C., more preferably at 20 to 55° C., more preferably at 25 to 45° C., most preferred at a temperature of 30 to 35° C., in particular 30° C. In certain embodiments, the reducing step ii) is carried out at a temperature of 10° C. to reflux.

In preferred embodiments the reaction time in the reducing step ii) is 4 to 144 hours and is e.g. controlled by in process controls, for example via HPLC. A further preferred reaction time in the reducing step ii) is 4 to 72 hours. In the case of using a hydrogen transfer agent, a preferred reaction time is 4 to 24 hours. In general, it is however important to determine the time necessary for the reaction based on in-process testing of the reaction in step ii). Thus the reaction completion should be monitored by in-process sampling, for example by HPLC.

After the hydrogenation, the batch can be cooled to about 10 to 30° C., filtered and stirred with 4 to 8, preferably 6 wt. parts of water per wt. part oripavine. Afterwards, the batch can be adjusted to pH 7 to 9, preferably 7.4 to 8.4, further preferably 7.8 to 8.2 with sodium hydroxide.

It is also possible in certain embodiments that the oxymorphone is isolated as base or salt and reduced again according to step ii) and optionally isolated according to step iii).

In step iii) the treatment agent preferably is selected from the group consisting of HCl, sulfuric acid, tartaric acid, citric acid, phosphoric acid and HBr.

The present method can further comprises a step iv) of purifying the oxymorphone salt obtained from step ii), wherein the oxymorphone salt is treated with a base to precipitate free oxymorphone base. For this reaction, the base can be selected from NaOH, KOH and NH$_4$OH.

The base can be prepared with the use of a purification agent selected from the group consisting of 1-butanol, carbon and encapsulated carbon, isopropyl alcohol, 2-butanol, 1 propanol, filter aid, methanol and ethanol. In certain embodiments, the purification step iv) is carried out at a temperature of 10 to 70° C. or from 10° C. to reflux.

After the purification, the purified oxymorphone can be precipitated at a pH of 6.5 to 9.5, preferably 7.4 to 8.4, at a temperature of 15 to 70° C., preferably 45 to 55° C. After cooling to about 5 to 30° C., preferably about 20° C., the precipitate can be held for at least one hour and filtered. The wet cake then can preferably be washed with water. Optionally, the purified oxymorphone can be dried under vacuum and elevated temperature before it is further processed.

In certain embodiments, the base that has been purified is converted to a pharmaceutically acceptable salt of oxymorphone, for example using HCl, sulfuric acid, tartaric acid, citric acid, phosphoric acid or HBr.

Further disclosed in the present invention is a product obtainable by the present method, as well as a composition comprising the oxymorphone or salt thereof produced by the present method. Also disclosed is a composition comprising oxymorphone or a salt thereof, preferably oxymorphone HCl or oxymorphone as a base that has a content of alpha-beta-unsaturated ketones <10 ppm and a content of 8,14-dihydroxydihydromorphinone >10 ppm, >25 ppm or >50 ppm, or >100 ppm, or >250 ppm, or 500 ppm and up to and including 1500 ppm. In certain embodiments, the composition has less than 0.15 wt. % 10-Hydroxyoxymorphone, more preferably less than 0.10 wt. %, and/or less than 0.15 wt. % pseudooxymorphone, more preferably less than 0.10 wt %, and/or less than 0.15 wt. % 6-alpha oxymorphol, more preferably less than 0.10 wt. %, and/or less than 0.15 wt. % 6-beta oxymorphol, more preferably less than 0.10 wt. %, and/or less than 0.10 wt. % of other impurities. The composition can comprise less than 2 wt. % impurities in total, and preferably comprises less than 1 wt. % total impurities. Other alpha beta unsaturated ketones such as codeinone, morphinone or 14-hydroxycodeinone, are each at levels less than 10 ppm as measured, for example, by HPLC.

In certain embodiments, levels of >0.01 wt. % of 8,14-dihydroxydihydromorphinone are allowed in the oxymorphone or its salt after step ii) as this enables an easier and faster production. In some embodiments levels >0.05 wt. % of 8,14-dihydroxydihydromorphinone, and in certain embodiments >0.1 wt. % of 8,14-dihydroxydihydromorphinone are allowed in the oxymorphone or its salt after step ii).

In addition, a pharmaceutical formulation is disclosed that comprises a composition according to the invention and a pharmaceutically acceptable carrier.

In certain embodiments, the composition can be used in the treatment of pain, e.g. to relieve moderate to severe pain.

With the present method, a number of polymorphs can be prepared, e.g. the ones disclosed in Example 6 as well the one disclosed in U.S. Pat. No. 7,851,482.

In the present invention also the new polymorph of form II in Example 6 is disclosed, which can be prepared by the present method.

Also disclosed is a method of polymorph conversion, wherein one polymorph, e.g. one that is not desirable, is converted into another polymorph by heating the polymorph in a solvent that does not dissolve or react with oxymorphone HCl, e.g. aqueous isopropanol, at a temperature in the range of 30° C. to 110° C. or up to the boiling point of the solvent or solvent mixture, preferably from 55° C. to 90° C., particularly preferably from 60° C. to 85° C. for more than 15 minutes, and then rapidly cooling the formed slurry to a temperature of −20° C. to 25° C. and filtering of the solids.

EXAMPLES

The present invention will now be described in detail with reference to several examples thereof. However, these examples do not limit the scope of the invention.

In the following examples, impurities were measured by HPLC. The measurement conditions are given in the following:

Analysis for 14-Hydroxymorphinone
Buffer: Dissolve 6.9 g of sodium phosphate monobasic monohydrate and 10.8 g of dodecyl sulfate, sodium salt into 2000 mL of deionized water. Mix until well dissolved.
Mobile Phase A
  Combine 1600 mL of Buffer with 400 mL of acetonitrile and 8.50 mL 10% NaOH. Mix well and filter.
Mobile Phase B
  Acetonitrile
Step 1, Collection of Eluent (with 14-Hydroxymorphinone):
  Column: Zorbax XDB C18 4.6 mm×50 mm, 3.5 μm
  Flow Rate: 2 mL/min
  Wavelength: 220 nm
  Range: 500 mAU
  Injection Volume: 10 μL
  Column Temperature: 40° C.
  Run Time: 17 minutes
  Gradient Conditions:

| Time (min) | % Mobile Phase A | % Mobile Phase B |
|---|---|---|
| 0.0 | 100 | 0 |
| 5.0 | 100 | 0 |
| 10.0 | 50 | 50 |
| 10.1 | 100 | 0 |
| 17.0 | 100 | 0 |

| Component | Approx. RT (min) | Approx. RRT |
|---|---|---|
| 14-Hydroxymorphinone | 2.4 | 0.7 |
| Oxymorphone | 3.6 | 1.0 |

RT = retention time
RRT = relative retention time

Step 2, Recovery:
  Column: Phenomenex Gemini 3µ C$_6$-Phenyl 4.6 mm×50 mm, 110 A pore size
  Flow Rate: 2 mL/min
  Wavelength: 220 nm
  Range: 500 mAU
  Injection Volume: 100 µL
  Column Temperature: 40° C.
  Run Time: 10 minutes
For Recovery, use 100% Mobile Phase A with no gradient.
Analysis for Pseudooxymorphone
  Mobile Phase: Accurately weigh 5.4 grams of potassium phosphate monobasic, and dissolve with 1600 mL of deionized water. Mix until well dissolved, then add 400 mL of acetonitrile and 3.0 mL of triethylamine and mix well. Adjust the pH of this solution to 7.95±0.05 units, using 2.5M KOH. Filter the solution through a 1 µm paper disc filter.

| Column: | Phenomenex Gemini C$_6$-Phenyl 4.6 mm × 250 mm, 5 µm, 110A pore size | |
|---|---|---|
| Flow Rate: | 1.2 mL/min | |
| Wavelength: | 220 nm | |
| Range: | 1,000 mAU | |
| Injection Volume: | 10 µL | |
| Column Temperature: | 50° C. | |
| Run Time: | 25 minutes | |
| Component | Approx. RT (min) | Approx. RRT | RRF |
| Oxymorphone | 9.8 | 1.0 | 1.00 |
| Pseudooxymorphone | 15.1 | 1.5 | 0.94 |

RT = retention time
RRT = relative retention time
RRF = relative response factor Analysis for Other Impurities
  Mobile Phase: Accurately weigh 5.4 grams of potassium phosphate monobasic, and dissolve with 1600 mL of deionized water. Mix until well dissolved, then add 400 mL of acetonitrile and 3.0 mL of triethylamine and mix well. The pH of this solution should be very close to 7.50, (+/−0.05. units). If necessary, adjust the pH of this solution to 7.50 (±0.05 units) using either phosphoric acid or potassium hydroxide. Filter the solution through a 1 µm paper disc filter.

| Column: | Phenomenex Gemini C$_6$-Phenyl 4.6 mm × 250 mm, 5 µm, 110A pore size | |
|---|---|---|
| Flow Rate: | 1.2 mL/min | |
| Wavelength: | 220 nm | |
| Range: | 1,000 mAU | |
| Injection Volume: | 10 µL | |
| Column Temperature: | 50° C. | |
| Run Time: | 25 minutes | |
| Component | Approx. RT (min) | Approx. RRT | RRF |
| 8,14-Dihydroxy dihydropmorphone | 4.2 | 0.68 | 0.97 |
| Oxymorphone | 6.2 | 1.00 | 1.00 |

RT = retention time
RRT = relative retention time
RRF = relative response factor Example 1

Steps i) and ii): Crude Oxymorphone

Water (75.0 g) and 90% formic acid (255.0 g, 4.986 mol) were charged to a 2 L flask. The resulting solution was stirred at room temperature. Oripavine (150.0 g, 0.504 mol) was added and stirred until a clear solution was obtained. The solution temperature was brought to 30° C. and 35% hydrogen peroxide (25.7 g, 0.264 mol. 50% of the total amount needed) was added drop-wise in 15 min. The resulting solution was stirred for 1 h at 30-33° C., followed by the addition of a second portion of 35% hydrogen peroxide in 15 min (26.3 g, 0.271 mol. total hydrogen peroxide, 1.06 equivalents of oripavine). The progress of the reaction after 3 h at 30° C. was analyzed by HPLC.

Once the oxidation is complete, the reaction solution was transferred to a 2 L stainless steel hydrogenation vessel and 5% Pd/C was added (9.2 g, 50.91% wet. 3% loading by dry weight vs. oripavine), followed by addition of isopropyl alcohol (IPA) (353 g). The mixture was hydrogenated at 30° C. under 45-50 psig of hydrogen for 16 h. The HPLC reaction completion test showed the unreacted 14-hydroxymorphinone at 0.05%. The catalyst was removed by filtration, washed with water (2×100 ml) and the filtrate diluted with water (900 ml). 50% NaOH was added slowly to the filtrate to precipitate crude oxymorphone, potentially containing oxymorphone salt, while maintaining the solution temperature at <50° C. First the pH was adjusted to ~8 and the batch was stirred for 30 min. Additional 50% NaOH was added to adjust the pH to 9.1. The resulting slurry was cooled to room temperature and stirred for 1 h. The oxymorphone was isolated by filtration. The wet cake was washed with water (3×100 ml) then with IPA (100 ml) to give a light tan colored solid (153.8 g, wet). The calculated yield of oxymorphone was 93.0% after correction for solvent content in the wet cake.

Step iii) Crude Oxymorphone HCl

The wet oxymorphone base from step ii) (150.6 g wet. 138.4 g dry. 0.459 mol), 90% formic acid (226.3 g. 4.425 mol) and IPA (237.1 g) were charged to a 2 L stainless steel hydrogenation vessel followed by addition of 5% Pd/C (9.0 g, 50.91% wet. 3% loading by dry weight vs. wet oxymorphone). The resulting mixture was hydrogenated at 70° C. under 15 psig of hydrogen. After 24 h of hydrogenation, a reaction completion test was performed. The results showed the 14-hydroxymorphinone level at 3 ppm. The reaction was cooled to 25° C., after which the catalyst was removed by filtration. Additional IPA (474.2 g) was added to the filtrate and the mixture was stirred at room temperature. 31% HCl (75.9 g. 0.645 mol) was added to adjust the pH to 1.29. The resulting slurry was cooled to 0-10° C., stirred for 2 h, filtered and washed with cold 85% IPA (3×40 ml) to give an off-white solid (185.2 g, wet). The calculated yield of oxymorphone HCl was 85.4% after correction for solvent content in the wet cake.

HPLC Impurity Results

| Oxymorphone Base, Crude | | Oxymorphone HCl, Crude | |
|---|---|---|---|
| RRT 0.51 | 0.06% | RRT 0.51 | 0.01% |
| RRT 0.56 | 0.05% | RRT 0.56 | 0.07% |
| RRT 0.63 | 0.40% | RRT 0.63 | 0.06% |
| 8,14-Dihydroxy-dihydromorphinone | 0.27% | 8,14-Dihydroxy-dihydromorphinone | 0.17% |
| RRT 0.72 | 0.05% | RRT 0.72 | Not detected |
| 14-Hydroxymorphinone | 0.05% | 14-Hydroxymorphinone | 2 ppm |
| RRT 1.77 | 0.05% | RRT 1.76 | 0.07% |

Example 2

Steps iv) Oxymorphone Base Purified

Oxymorphone HCl crude wet, made the same way as in Example 1, Step iii), (25.38 g. 20.99 g dry. 0.062 mol) and water (126.93 g) were charged to a 500 ml flask and stirred to dissolve. Activated carbon was added and the resulting mixture stirred at room temperature for 1 h, filtered, and then washed with water (15 ml). 1-butanol (10.5 g) was added to the filtrate. The mixture was stirred at 50° C. 50% NaOH was added to adjust the pH to 8.16. The resulting slurry was cooled to 20° C. and stirred for 1 h. Oxymorphone base purified was isolated by filtration and washed with water. The wet cake was tan colored, weighed 18.22 g after drying. The molar yield of oxymorphone base purified was 96.8%.

HPLC Impurity Results

| Oxymorphone HCl Crude | | Oxymorphone Base Purified | |
|---|---|---|---|
| RRT 0.56 | 0.04% | RRT 0.56 | 0.01% |
| RRT 0.63 | 0.10% | RRT 0.63 | 0.05% |
| 8,14-Dihydroxy-dihydromorphinone | 0.20% | 8,14-Dihydroxy-dihydromorphinone | 0.09% |
| Pseudooxymorphone | 0.14% | Pseudooxymorphone | 0.04% |
| 14-Hydroxymorphinone | 1 ppm | 14-Hydroxymorphinone | 4 ppm |

Example 3

Step v) Oxymorphone HCl

Oxymorphone base purified wet, made the same way as in Example 2, Step iv), (122.7 g wet. 97.1 g dry. 0.322 mol), IPA (412.7 g) and water (47.2 g) were charged to a 2 L 3-necked jacketed round bottomed flask and stirred at 55° C. under nitrogen. 31% HCl (39.3 g. 0.334 mol) was added slowly to adjust the pH to 2.08. The resulting slurry was heated to 73° C., held for 1 h, followed by fast cooling to 4° C. (0-10° C.). After holding at 4° C. for 2 h, oxymorphone HCl wet was isolated, washed with cold 85% IPA. The wet cake was off-white, weighed 119.8 g and had 13.8% solvent. The calculated molar yield of Oxymorphone HCl was 94.9%. Oxymorphone HCl wet (93.5 g) was dried in a vacuum oven at 55° C. under full vacuum with nitrogen purge for 22 h to give a white solid.

HPLC Impurity Results

| Oxymorphone Base Purified | | Oxymorphone HCl | |
|---|---|---|---|
| RRT 0.56 | 0.05% | RRT 0.56 | 0.02% |
| RRT 0.63 | 0.08% | RRT 0.63 | Not detected |
| 8,14-Dihydroxy-dihydromorphinone | 0.03% | 8,14-Dihydroxy-dihydromorphinone | 0.02% |
| 14-Hydroxymorphinone | 7 ppm | 14-Hydroxymorphinone | 4 ppm |

Example 4

Step iii) Oxymorphone HCl Crude Via Transfer Hydrogenation

Oxymorphone crude wet, made the same way as in Example 1, Steps i) and ii), (150.2 g wet. 130.7 g dry. 0.43 mol. 14-hydroxymorphinone 398 ppm; 8,14-dihydroxydihydromorphinone 768 ppm) was dissolved in 90% formic acid (223.1 g. 4.36 mol) and isopropanol (IPA) (300 ml). 5% Pd/C (56% wet. 7.5 g.) was added. The mixture was heated under reflux for 48 h, cooled to room temperature, filtered to remove catalyst, and rinsed with 80% aq. IPA (2×30 ml). More IPA (600 ml) was added to the filtrate. To the mixture was added 32% HCl (69.3 g) to adjust its pH to 1.42. The resulting slurry was cooled to 0-10° C., stirred for 2 h, filtered, washed with cold 80% aqueous IPA. The wet cake was dried at 65° C. under vacuum to get was 133.8 g of oxymorphone HCl. HPLC analysis showed it had 2 ppm 14-hydroxymorphinone and 226 ppm 8,14-dihydroxydihydromorphinone.

Example 5

Making Low ABUK Oxymorphone HCl from Oripavine without Isolating Oxymorphone Base Crude Oripavine (40.0 g. 0.135 mol) was dissolved in 90% formic acid (68.7 g. 1.34 mol) and IPA (20 ml) and stirred at 30° C. 35% $H_2O_2$ (13.9 g. 0.143 mol) was added drop wise. The oxidation reaction finished after 4 h. 5% Pd/C (54.6% wet. 2.5 g) and isopropanol (IPA) (80 ml) were added to the oxidation solution and the mixture was hydrogenated at 70° C. under 12-20 psig of hydrogen for 20 h. The catalyst was filtered off (which is an optional step). More catalyst was added (2.5 g) and the hydrogenation was continued for another 46 h, after which HPLC showed no detectable 14-hydroxymorphinone and 0.48 area % of 8,14-dihydroxydihydromorphinone. The reaction mixture was filtered, followed by addition of more IPA (160 ml) and stirred at 50° C. 31% HCl (14.1 g. 0.120 mol) was added to pH=1.75. The slurry was cooled to 0-10° C., stirred for 2 h, filtered and washed with cold 85% aq. IPA. The isolated wet oxymorphone HCl was dried at 60° C. under vacuum to get an off-white solid 33.3 g, yield 73.3%. HPLC results: 14-hydroxymorphinone, 8 ppm; 8,14-dihydroxydihydromorphinone, 1703 ppm.

Example 6

Oxymorphone HCl Polymorphic Forms were Prepared by the Present Method

Preparation of Form I 38.9 g oxymorphone base was suspended in 235 ml aqueous ethanol (94% w/w) at 50-60° C. 15.5 g HCl (32%) was added to pH 3.15. The resulting slurry was cooled to 10° C., stirred for 2 h, filtered off and washed with ethanol and dried.

Preparation of Form II 15.0 g oxymorphone HCl was dissolved in 60 g aqueous IPA (75% w/w) at 60-70° C. and then the solution was cooled slowly to 0-10° C. The solids were filtered and dried.

Conversion of Form II to Form I

Form II oxymorphone HCl was heated in aqueous IPA (70-85% w/w) at 65° C. and above for 30 minutes or more. The slurry was cooled quickly to 0-10° C. and the solids were filtered off and dried. The isolated salt is Form I.

The polymorphs of oxymorphone HCl were determined on a Rigaku MiniFlex X-ray Powder Diffractometer instrument; X-ray radiation from Copper Cu at 1.054056 Å with $K_\beta$ filter.

Form I

Figure 1:
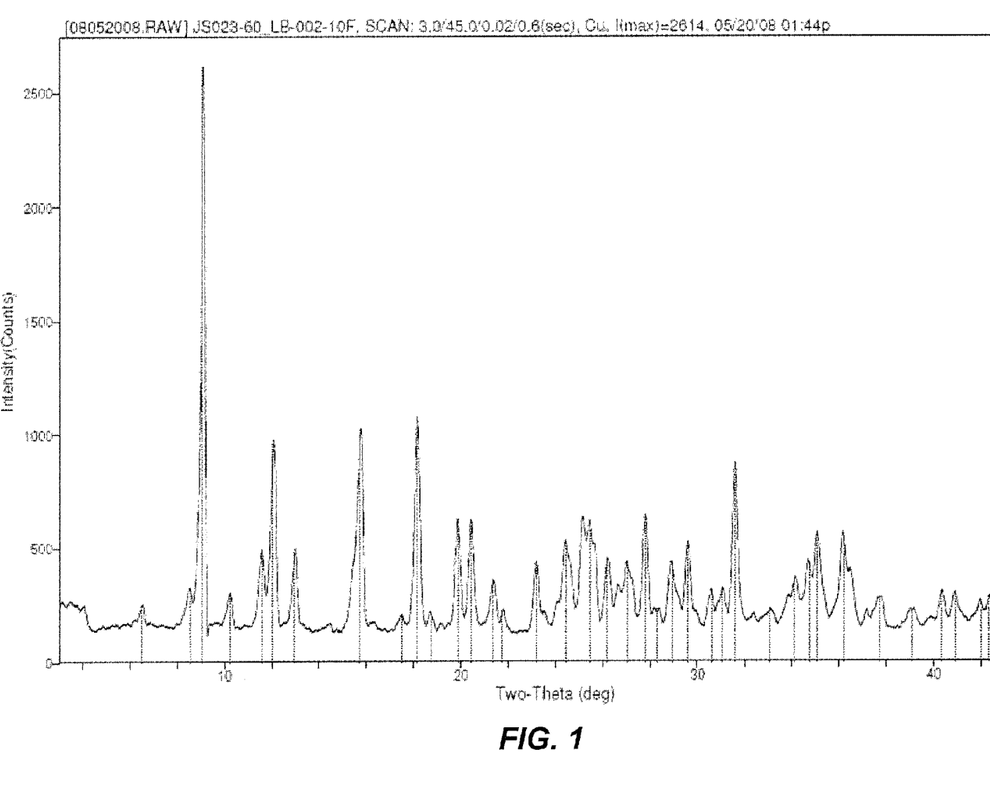
FIG. 1 shows an X-ray powder diffraction graph obtained for oxymorphone HCl polymorphic form I obtained in example 6.

For form I, the following peaks were obtained, and a graph of the measurement is shown in FIG. 1.

Peaks: 2-Theta (H %)

9.4 (100.0%), 10.3 (8.8%), 12.5 (4.5%), 13.2 (9.8%), 15.6 (3.3%), 16.7 (3.0%), 17.4 (9.2%), 18.9 (26.9%), 19.7 (7.0%), 20.6 (9.0%), 21.3 (1.1%), 22.6 (2.2%), 23.2 (1.3%), 23.8 (6.4%), 25.1 (47.7%), 26.9 (11.7%), 27.3 (2.4%), 28.4

(34.8%), 30.0 (1.3%), 30.5 (1.2%), 31.2 (5.4%), 32.3 (1.9%), 33.1 (0.7%), 34.5 (12.9%), 35.6 (3.4%), 36.5 (1.0%), 36.8 (1.7%), 37.5 (0.9%), 38.2 (5.0%), 39.2 (5.3%), 40.0 (2.0%), 41.9 (0.8%), 42.7 (0.9%), 43.7 (1.9%).

Form II

Figure 2:
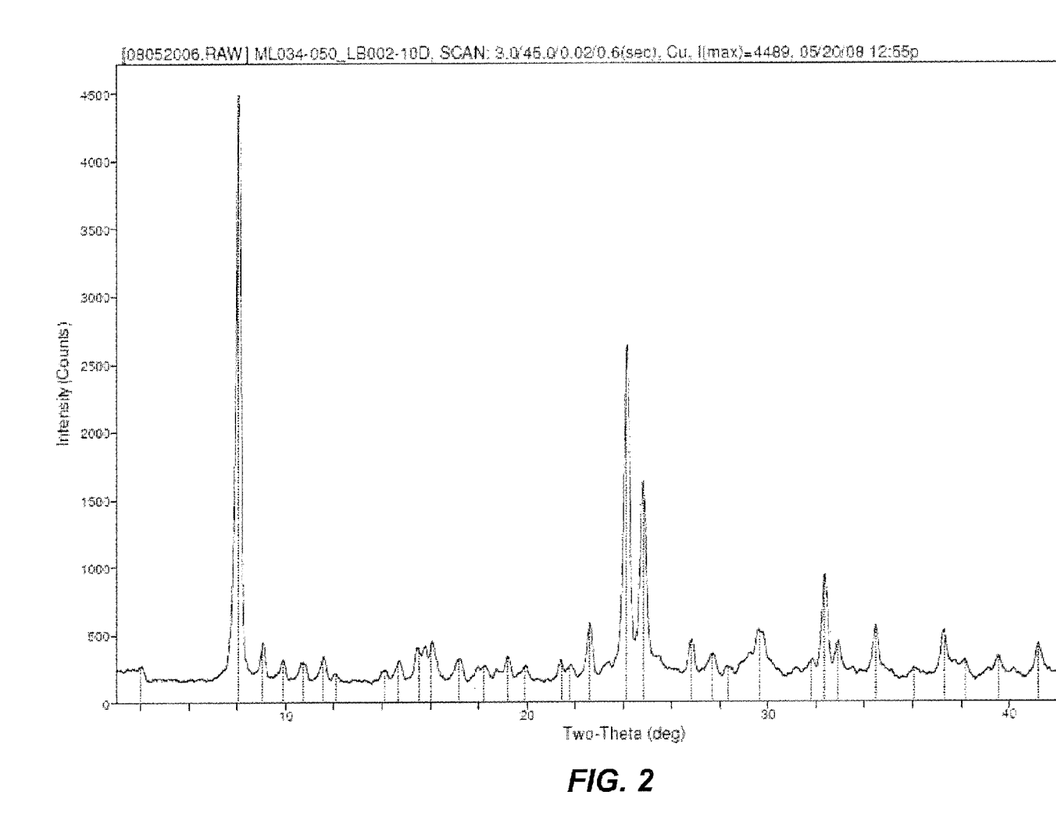
FIG. 2 shows an X-ray powder diffraction graph obtained for oxymorphone HCl polymorphic form II obtained in example 6.

For form II, the following peaks were obtained, and a graph of the measurement is shown in FIG. 2.
Peaks: 2-Theta (H %)
8.0 (100.0%), 9.0 (5.7%), 9.9 (3.2%), 10.7 (3.0%), 11.6 (4.2%), 12.1 (1.2%), 14.1 (1.8%), 14.7 (3.0%), 15.5 (5.1%), 16.0 (6.6%), 17.2 (3.8%), 18.2 (2.1%), 19.2 (3.7%), 19.9 (2.2%), 21.5 (3.3%), 21.8 (2.2%), 22.6 (8.9%), 24.1 (54.2%), 24.8 (30.0%), 26.8 (5.6%), 27.7 (3.6%), 28.4 (1.4%), 29.6 (7.7%), 31.8 (1.3%), 32.4 (16.6%), 32.9 (4.9%), 34.5 (8.5%), 36.1 (1.5%), 37.3 (7.3%), 38.2 (1.8%), 39.6 (3.9%), 41.2 (5.6%).

A method has been shown herein for preparing oxymorphone with low levels of alpha-beta-unsaturated ketones that does not require a complicated and tedious work-up after the production and isolation of crude oxymorphone in the conventional methods. With the present method, it is possible to obtain oxymorphone of high purity, particularly with low levels of 14-hydroxymorphinone, while allowing high levels of 8,14-dihydroxydihydromorphinone. Further, the presence of a strong acid in the oxidizing step i) is avoided, thus limiting the costs of the present process. Also a hydrogenation of the crude oxymorphone after the reducing step ii) can be avoided, leading to less costs and problems associated with the usage of a hydrogenation treatment for purification as disclosed in US 2008/0146601.

Also disclosed is a method of precipitating an oxymorphone salt from aqueous isopropyl alcohol which does not require a humidification of the vacuum during drying to remove water and solvent. In addition, a method is disclosed for producing oxymorphone hydrochloride having less than 10 ppm 14-hydroxymorphinone comprising exposing a starting material of oxymorphone or oxymorphone hydrochloride to gaseous hydrogen under reducing conditions in a strongly acid water and alcohol solvent as a reaction medium at a temperature in the range from 60 to 70° C., subsequently forming crystalline oxymorphone hydrochloride, and removing residual alcohol molecules from within the crystal structure of the crystalline oxymorphone hydrochloride without exposing the oxymorphone hydrochloride to water vapor.

Further disclosed is the purification of Oxymorphone by precipitating Oxymorphone free base by not using more than 1.5 equivalents, preferably less than 1.1 equivalents, particularly preferably 1.0 equivalents of base, as the use of more equivalents could otherwise lead to salt in the Oxymorphone product.

All references cited in this specification are herewith incorporated by reference in their entirety.

The present method has been described in detail with reference to certain embodiments and specified by examples. However, a skilled person will acknowledge that also other modifications, changes, or similar alterations can be made to the present invention without deviating from the spirit of the invention.

What is claimed is:

1. A method of preparing an oxymorphone salt, comprising:
    i) oxidizing oripavine to obtain 14-hydroxymorphinone;
    ii) reducing the 14-hydroxymorphinone to obtain oxymorphone; and
    iii) treating the oxymorphone from ii) with an acid to produce an oxymorphone salt
        without prior isolation of oxymorphone as a free base after reducing step ii), wherein:
        (1) the reducing step ii) proceeds without the use of an additional acid;
        (2) the oxymorphone produced in step ii), the oxymorphone salt produced in step iii), or both the oxymorphone produced in step ii) and the oxymorphone salt produced in step iii) comprise less than 10 ppm alpha-beta unsaturated ketones; and
        (3) levels of >10 ppm of 8,14-dihydroxydihydromorphinone are allowed in the oxymorphone produced in step ii) and/or its salt produced in step iii).

2. The method of claim 1, wherein the oxymorphone produced in step ii), its salt produced in step iii), or both the oxymorphone produced in step ii) and its salt produced in step iii) have a content of 8,14-dihydroxydihydromorphinone >10 ppm.

3. The method of claim 1, wherein the reducing step ii) comprises a hydrogenation.

4. The method of claim 3, wherein no second hydrogenation is carried out.

5. The method of claim 1, wherein the 14-hydroxymorphinone is not isolated before reducing step ii).

6. The method of claim 1, wherein step i) is carried out in the absence of an acid with a pKa<0.

7. The method of claim 1, wherein the reducing step ii) comprises reducing 14-hydroxymorphinone at a pH>1.

8. The method of claim 1, wherein the reducing step ii) comprises adding a hydrogen transfer agent.

9. The method of claim 8, wherein the hydrogen transfer is carried out in the presence of a metal catalyst selected from the group consisting of transition metals in any form on carbon, BaSO4, alumina, transition metal oxides, transition metal salts, phosphine ligand metal complexes, and mixtures thereof.

10. The method of claim 1, wherein the reducing step ii) is carried out with hydrogen in the presence of a metal catalyst selected from the group consisting of transition metals on carbon, transition metal oxides, transition metal salts, phosphine ligand metal complexes, and mixtures thereof.

11. The method of claim 9, wherein additional catalyst is charged during the reducing step ii).

12. The method of claim 1, wherein the salt obtained in step iii) is further purified in a purifying step iv) by precipitating free oxymorphone base by treating the salt with base.

13. The method of claim 12, wherein the base is prepared with the use of a purification agent selected from the group consisting of 1-butanol, carbon and encapsulated carbon, isopropyl alcohol, 2-butanol, 1 propanol, filter aid, methanol and ethanol.

14. The method of claim 12, wherein the base is converted to a pharmaceutically acceptable salt of oxymorphone.

15. The method of claim 10, wherein additional catalyst is charged during the reducing step ii).

16. The method of claim 1, wherein both the oxymorphone produced in step ii) and the oxymorphone salt produced in step iii) comprise less than 10 ppm alpha-beta unsaturated ketones.

* * * * *